United States Patent
Bootwala

(10) Patent No.: US 10,722,695 B2
(45) Date of Patent: *Jul. 28, 2020

(54) DILATION SYSTEM AND METHOD

(71) Applicant: DEPUY SYNTHES PRODUCTS, INC., Raynham, MA (US)

(72) Inventor: Zoher Bootwala, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 48 days.

This patent is subject to a terminal disclaimer.

(21) Appl. No.: 16/051,655

(22) Filed: Aug. 1, 2018

(65) Prior Publication Data

US 2018/0339142 A1 Nov. 29, 2018

Related U.S. Application Data

(63) Continuation of application No. 15/480,587, filed on Apr. 6, 2017, now Pat. No. 10,046,149, which is a continuation of application No. 14/290,582, filed on May 29, 2014, now Pat. No. 9,642,607.

(51) Int. Cl.
*A61M 29/00* (2006.01)
*A61B 5/04* (2006.01)
*A61B 17/02* (2006.01)

(52) U.S. Cl.
CPC ......... *A61M 29/00* (2013.01); *A61B 5/04001* (2013.01); *A61B 17/02* (2013.01); *A61B 2017/0225* (2013.01); *A61B 2560/0468* (2013.01)

(58) Field of Classification Search
CPC .............. A61B 17/1717; A61B 17/164; A61B 17/3421; A61M 29/00
See application file for complete search history.

(56) References Cited

U.S. PATENT DOCUMENTS

| | | |
|---|---|---|
| 1,331,737 A | 2/1920 | Ylisto |
| 3,667,474 A | 6/1972 | Lapkin et al. |
| 4,320,762 A | 3/1982 | Bentov |
| 8,313,430 B1 | 11/2012 | Pimenta |
| 8,728,162 B2 | 5/2014 | Akyuz |
| 2006/0106416 A1 | 5/2006 | Raymond et al. |
| 2006/0271096 A1 | 11/2006 | Hamada |
| 2007/0179602 A1 | 8/2007 | Wright |
| 2008/0039865 A1 | 2/2008 | Shaher et al. |
| 2013/0103103 A1 | 4/2013 | Mire et al. |

FOREIGN PATENT DOCUMENTS

WO 2006/058079 6/2006

*Primary Examiner* — Andrew Yang
(74) *Attorney, Agent, or Firm* — Dunlap Codding, P.C.

(57) ABSTRACT

A dilation system and method for accessing a surgical target site to perform surgical procedures. In one version, the dilation system includes a dilation assembly and an actuating mechanism. The dilation assembly comprises plurality of dilator segments. The actuating mechanism is operably associated with the dilator segments so as to cause the dilator segments to move from a collapsed state to an expanded state.

17 Claims, 8 Drawing Sheets

DILATION SYSTEM AND METHOD

CROSS-REFERENCE TO RELATED APPLICATION

This application is a continuation of U.S. application Ser. No. 15/480,587, filed on Apr. 6, 2017, which is a continuation of U.S. application Ser. No. 14/290,582, filed on May 29, 2014, the entirety of each being hereby expressly incorporated herein by reference.

BACKGROUND

Dilators are known devices for creating surgical access sites. Once an operative level is identified and an incision is created, dilators are used to create a surgical access site which is often followed by the use of a retractor or other specialized tools to create a surgical access corridor.

When accessing certain areas of a patient, it is desirable to avoid neural elements or nerves. For example, during a lateral approach to a patient's spine, a psoas muscle, which is located on either side of the spine, is separated in order to access the spine and, in particular, an intervertebral disc space or one or more vertebral bodies within a patient's spinal column. It is desirable to avoid neural elements or nerves of the lumbar plexus that lie within the psoas muscle during such procedures. The anterior third of the psoas muscle is typically considered a safe zone for muscle separation.

The neural elements or nerves of the psoas muscle may be mapped using a probe. In this manner, the most posterior neural or nerve free area of the psoas muscle may be located and identified. The probe may then be inserted through the psoas muscle via the most posterior neural or nerve free tissue area or through nearly any other region that is free of neural elements or nerves and toward the spine or into the intervertebral disc space in order to initiate safe tissue separation of the psoas muscle. Dilators are next placed over the probe to create and enlarge a surgical access site. Following the use of dilators, a retractor or other specialized tools are used to further enlarge the surgical access corridor.

DETAILED DESCRIPTION OF EXEMPLARY EMBODIMENTS

Figure 1:
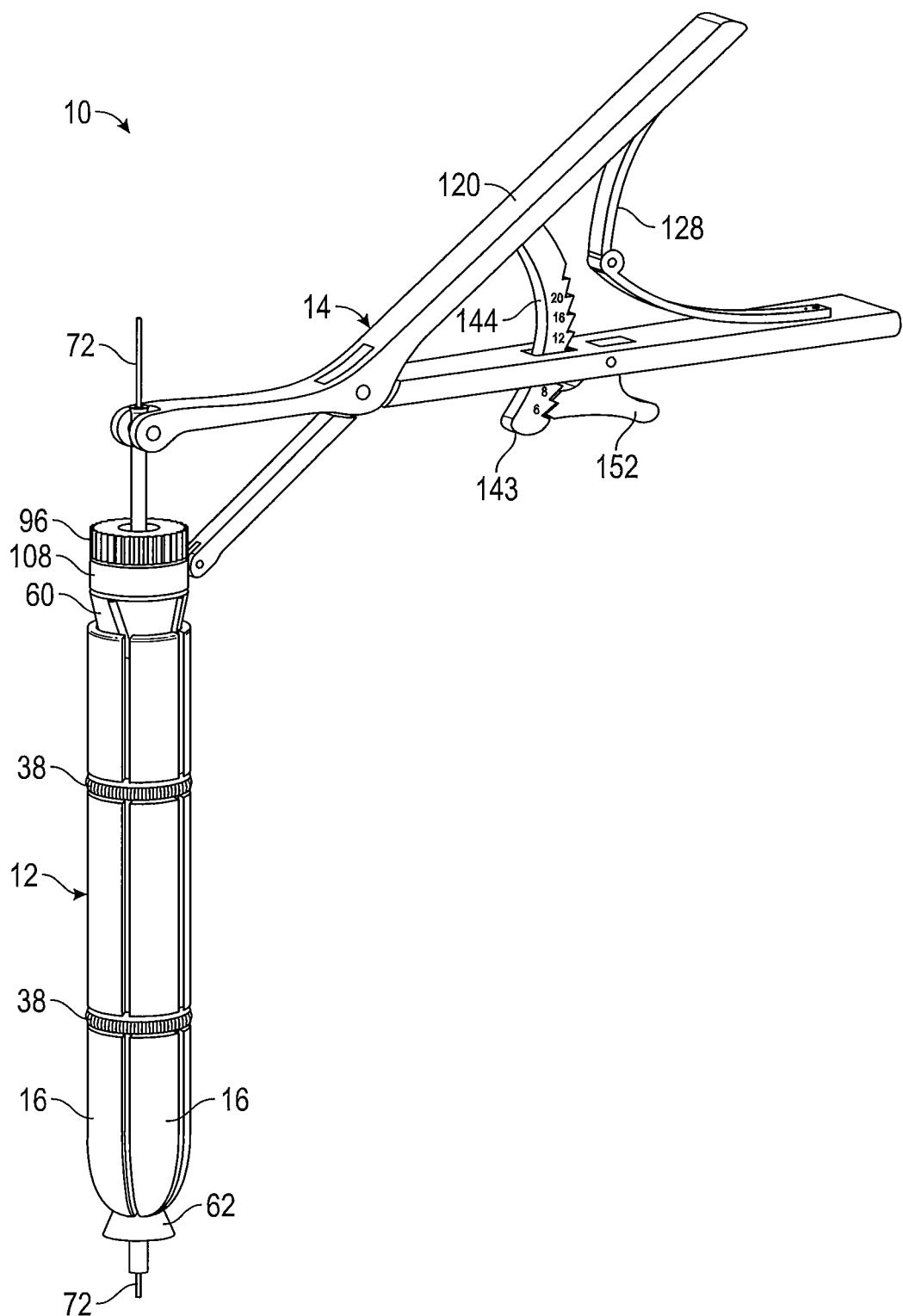
FIG. 1 is a perspective view of a dilation system constructed in accordance with the inventive concepts disclosed herein.

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "and combinations thereof" as used herein refers to all permutations or combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAAB-CCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The use of the terms "at least one" and "one or more" will be understood to include one as well as any quantity more than one, including but not limited to each of, 2, 3, 4, 5, 10, 15, 20, 30, 40, 50, 100, and all integers and fractions, if applicable, therebetween. The terms "at least one" and "one or more" may extend up to 100 or 1000 or more, depending on the term to which it is attached; in addition, the quantities of 100/1000 are not to be considered limiting, as higher limits may also produce satisfactory results.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

As used herein, the term "patient" is meant to include all organisms, whether alive or dead, including any species having soft tissues and bones. For example, a method according to the inventive concepts disclosed herein may be used to repair a spinal injury in a living human, horse, cow, sheep, cat, dog, and the like. In another example, a method according to the inventive concepts disclosed herein may be used in a non-living organism to train medical personnel in surgical techniques.

Certain exemplary embodiments of the invention will now be described with reference to the drawings. In general, such embodiments relate to dilation systems, and more particularly, to dilation systems for accessing a patient's spinal column. As generally understood by one of ordinary skill in the art, the dilation systems will be described in connection with accessing the spine to perform a surgical procedure, but the dilation systems will find use not only in orthopedic surgery, but in other surgical procedures in which a surgeon wishes to gain access to an internal cavity by cutting the skin and going through the body wall in order to keep the incision spread apart so that surgical instruments can be inserted. For example, the dilation systems may be used for anteriorly or posteriorly accessing the spine, for accessing the lumbar, thoracic, or cervical region of the spine, or for accessing nearly any other part of the body.

Referring to FIGS. 1, 2A, 2B, 3A, and 3B, a dilation system 10 is illustrated. The dilation system 10 may aid in performing surgical procedures and, more particularly, but not by way of limitation, may aid in accessing a surgical target site to perform surgical procedures. In some embodiments, the dilation system 10 may be used to create an initial corridor within a patient (e.g., 4-10 mm) which may be expanded to a desired diameter (e.g., 16-22 mm) without inserting any additional instruments. In some embodiments, the dilation system 10 may be used in combination with a guide, such as a K-wire or a monitoring probe, as further described herein.

The dilation system 10 includes a dilator assembly 12 and an actuating mechanism 14. The dilator assembly 12 may include a plurality of dilator segments 16. The actuating mechanism 14 is capable of moving the dilator segments 16 radially outwardly in a way to cause the dilator segments 16 to move between a collapsed state (FIGS. 1, 2A, and 3A) and an expanded state (FIGS. 2B and 3B) such that, in use, an initial corridor within a patient may be expanded to a desired diameter.

The dilator assembly 12 may include two or more dilator segments 16. For example, the dilator assembly 12 may include any number of dilator segments 16, such as, for example, two, three, four, and the like. The dilator assembly 12 is illustrated herein as having four dilator segments 16. The contour of the dilator segments 16, when assembled, may form a generally circular cylinder having a bore 20 extending the length of the dilator segments 16 from a proximal end 22 to a distal end 24 of the dilator assembly 12. It will be appreciated, however, that the dilator segments 16 may be configured to form other shapes, such as an oval shaped cylinder.

Figure 4:
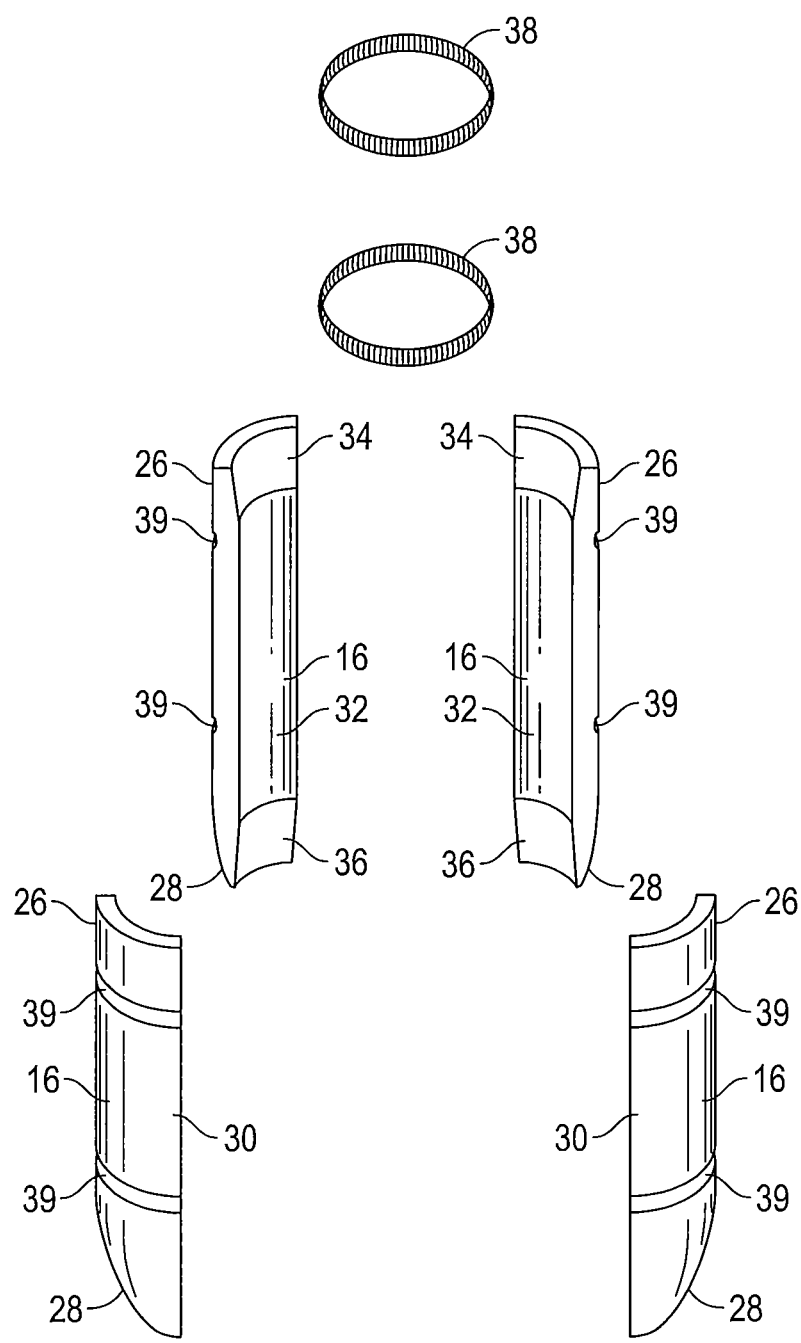
FIG. 4 is an exploded, perspective view of a dilator assembly.

Referring to FIG. 4, each dilator segment 16 may be a generally arc-shaped member having a proximal end 26, a distal end 28, an outer side 30, and an inner side 32. Each dilator segment 16 has a proximal tapered surface 34 extending from the proximal end 22 toward the distal end 24 and a distal tapered surface 36 extending from the distal end 24 toward the proximal end 22. The proximal tapered surfaces 34 and the distal tapered surfaces 36 are generally configured so that components of the actuating mechanism 14 may contact and slide along the proximal tapered surfaces 34 and the distal tapered surfaces 36 in a manner to be described below. In one embodiment, the proximal tapered surfaces 34 and the distal tapered surfaces 36 are generally arc shaped.

The dilator segments 16 may be machined, molded or extruded and machined from materials including, but not limited to, stainless steel, anodized aluminium, polyether ether ketone (PEEK), carbon fiber composite, and/or any biocompatible material suitable to maintain the shape and function of the components.

Tension may be applied to the dilator segments 16 by one or more constrictors 38 to bias the dilator segments 16 in the collapsed state. Constrictors 38 may be positioned about the dilator segments 16 such that, when in the collapsed state, the dilator segments 16 form the circular cylinder. For example, one or more constrictors 38 in the form of a ring may be positioned about an outer surface 36 of each dilator segment 16. In some embodiments, constrictors 38 may be positioned within a groove 39 on the outer side 30 of the dilator segments. Constrictors 38 may be positioned between the proximal end 26 and the distal end 28 of the dilator assembly 12. Exemplary constrictors 38 include, but are not limited to, elastic rings, donut springs, expansion springs, and/or the like.

Figure 3A:
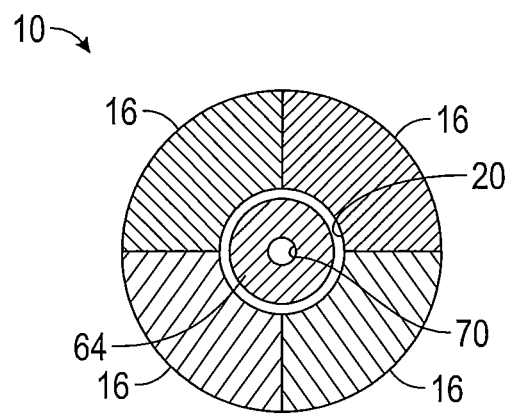
FIG. 3A is a cross sectional view taken along line 3A-3A of FIG. 2A.
Figure 3B:
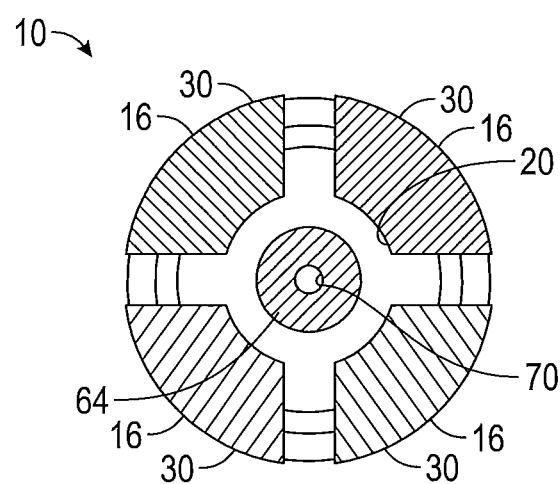
FIG. 3B is a cross sectional view taken along line 3B-3B of FIG. 2B.

Referring to FIGS. 3A and 3B, with the dilator assembly 12 in the collapsed state, the dilator segments 16 may form a circular cylinder having the bore 20 extending there through, as illustrated in FIG. 3A. In the collapsed state, the dilator segments 16 may be configured so that the dilator segments 16 cooperate to form a dilator of a desired diameter.

FIG. 3B illustrates the dilator assembly 12 in the expanded state wherein the dilator segments 16 are moved radially outward relative to the collapsed state whereby the outer side 30 of the dilator segments 16 cooperate to form a dilator of a desired diameter which is greater than the diameter of the dilator in the collapsed state. In some embodiments, the dilator segments 16 move uniformly away from the longitudinal axis. In some embodiments, the dilator segments 16 may be moved from the longitudinal axis at different distances so that the dilator assembly 12 expands a greater amount in a selected direction.

Figure 5:
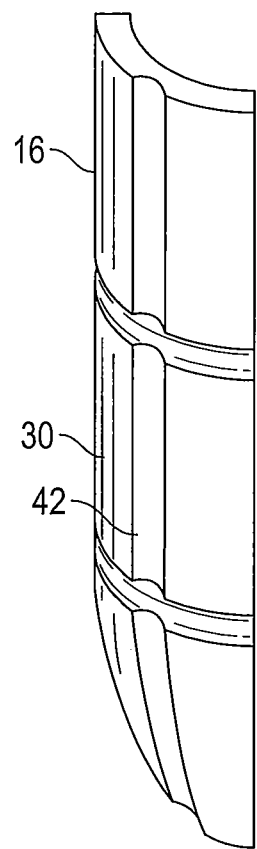
FIG. 5 is a perspective view of one version of a dilator segment.
Figure 6:
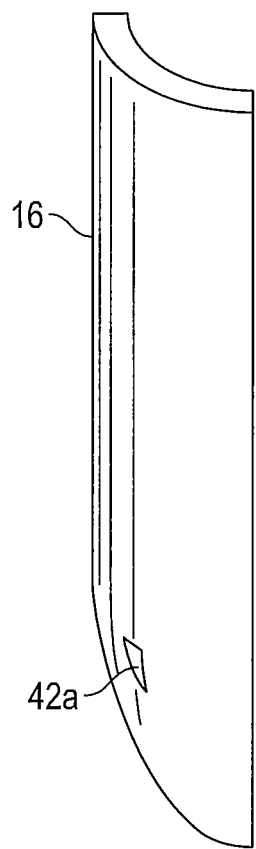
FIG. 6 is a perspective view of another version of a dilator segment.

To permit nerve monitoring for the purpose of determining the location of nerves or neural structures relative to the each of the dilator segments 16 as they are advanced over a K-wire (not shown) towards or positioned at or near the surgical target site and as they are moved to the expanded state, one or more of the dilator segments 16 may be configured to receive a probe (not shown). For example, the dilator segments 16 may include a channel 42 (FIG. 5) formed at or near the outer side 30 of the dilator segments 16 and extending the length of the dilator segments 16 for receiving a probe (not shown). Alternatively, as shown in FIG. 6, the one or more of the dilator segments 16 may include an electrode 42a to enable monitoring of nerves. The dilator segments 16 may be equipped with the electrodes 42a via any number of suitable methods, including but not limited to providing electrically conductive elements within the walls of the dilator segments 16 such as by manufacturing the dilator segments 16 from plastic or similar material capable of injection molding or manufacturing the dilators from aluminum (or similar metallic substance) and providing outer insulation layer with exposed regions (such as by anodizing the exterior of the aluminium dilator). The dilator segments 16 may include a corresponding connector point for connecting the electrode probe 42a to neural monitoring equipment. In another version, the electrodes may be adhered to the dilator segments 16 by a sticky probe or conductive epoxy ink.

Figure 2A:
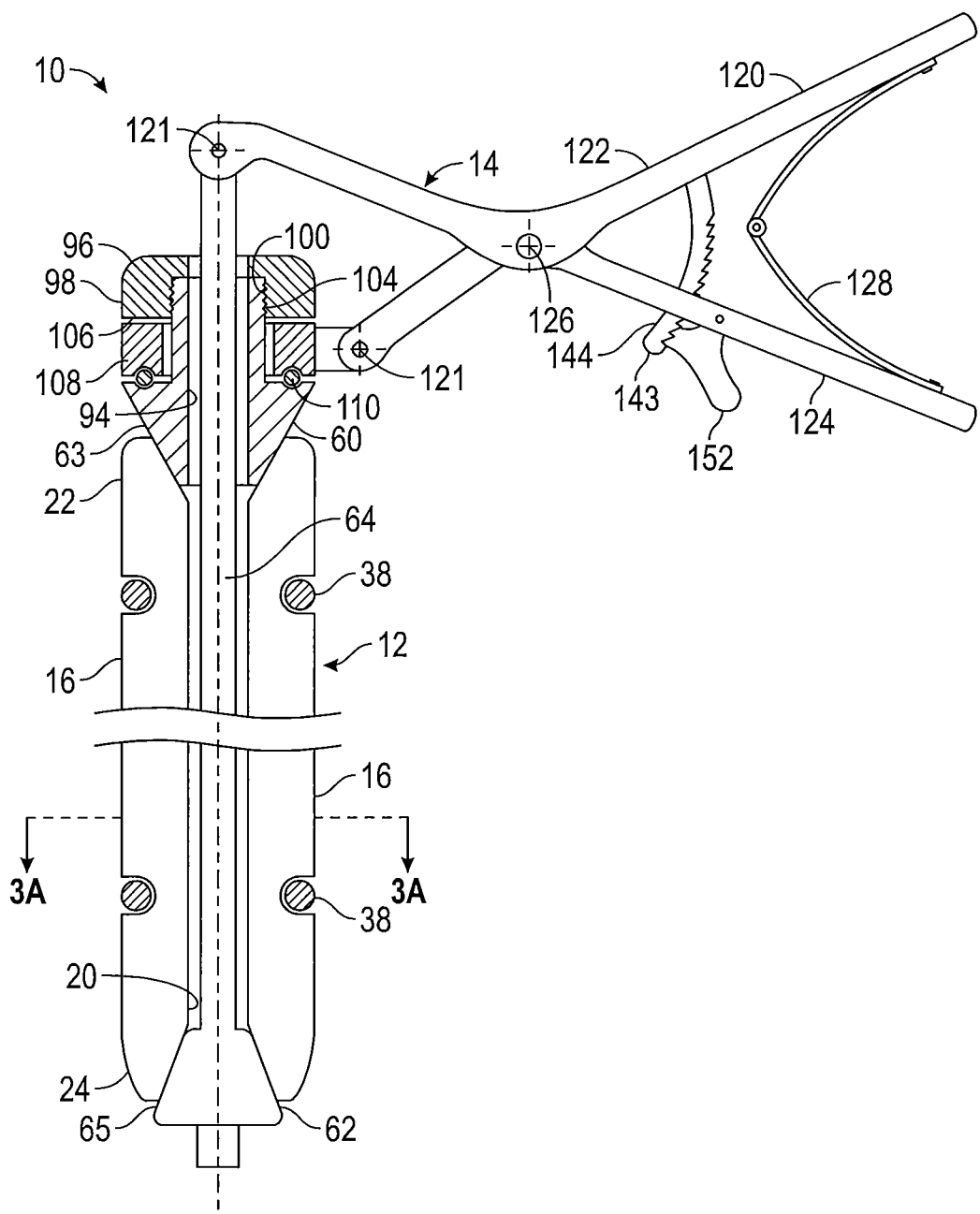
FIG. 2A is a partial cross sectional, side elevational view of the dilation system of FIG. 1 shown in a collapsed state.
Figure 2B:
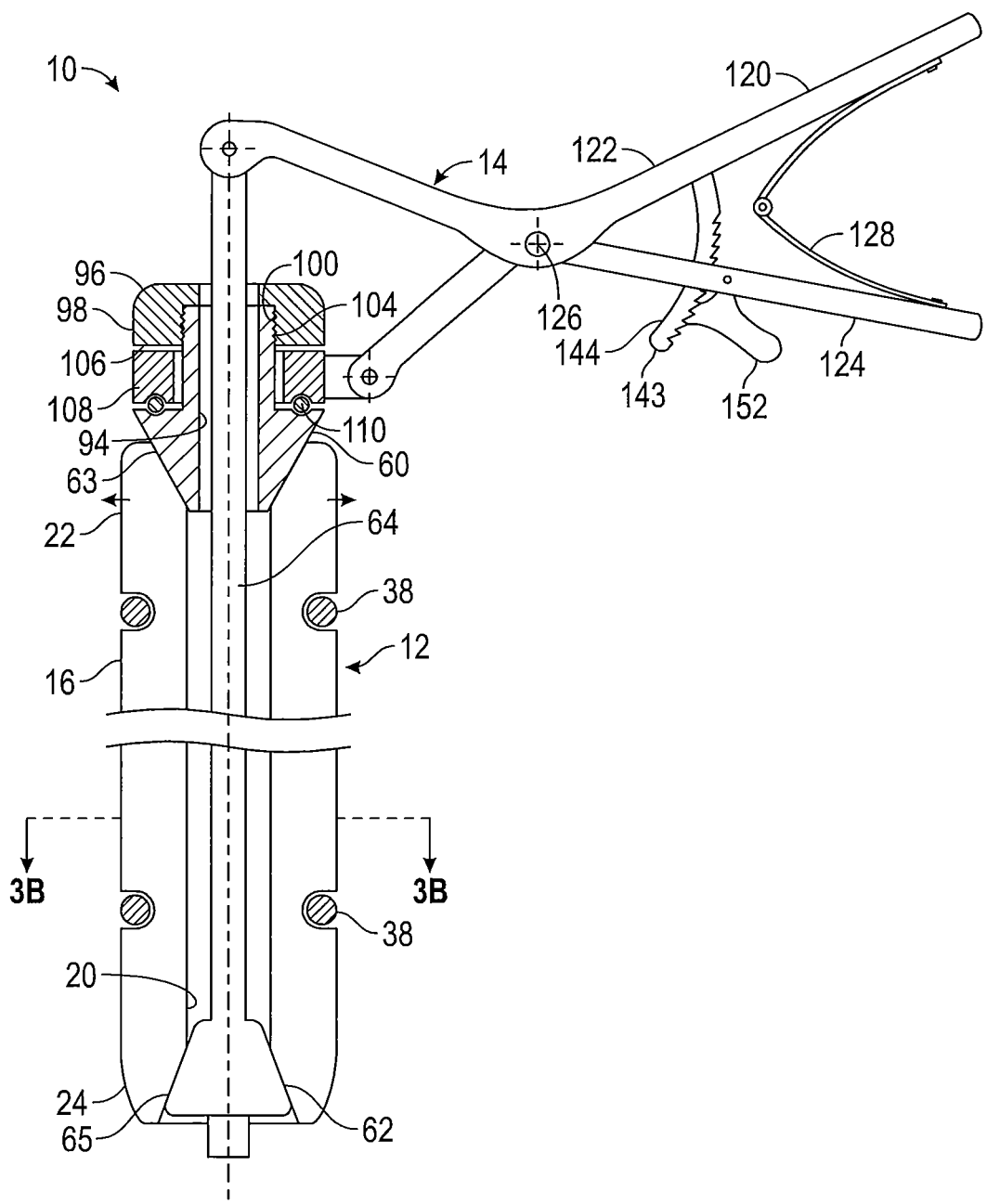
FIG. 2B is a partial cross sectional, side elevational view of the dilation system of FIG. 1 shown in an expanded state.

Referring to FIGS. 1, 2A, and 2B, the actuating mechanism 14 is used to move the dilator segments 16 from the collapsed state to the expanded state. The actuating mechanism 14 may include an upper wedge 60 and a lower wedge 62 axially moveable relative to one another. Generally, the upper wedge 60 is a conically shaped member with a tapered surface 63 corresponding to the proximal tapered surface 34 of the dilator segments 16 such that the tapered surface 63 of the upper wedge 60 is slidable along the proximal tapered surface 34 of the dilator segments 16. Similarly, the lower wedge 62 is a conically shaped member with a tapered surface 65 corresponding to the distal tapered surface 36 of the dilator segments 16 such that the tapered surface 65 of the lower wedge 62 is slidable along the distal tapered surface 36 of the dilator segments 16. Relative axial movement of the upper wedge 60 and the lower wedge 62 toward one another in turn causes the dilator segments 16 to move from the collapsed state (FIG. 2A) to the expanded state (FIG. 2B).

The actuating mechanism 14 further includes an elongated rod 64 extending from the lower wedge 62. The elongated rod 64 extends from the lower wedge 62, through the bore 20 of the dilator assembly 12, and through and beyond the upper wedge 60. In some embodiments, the lower wedge 62 may be integral to the elongated rod 64. In some embodiments, the lower wedge 62 may be connected to the elongated rod 64.

Referring to FIGS. 3A and 3B, in some embodiments, the elongated rod 64 may include a bore 70 extending the length of the elongated rod 64. In some embodiments, the bore 70 may be sized to receive a probe 72 (FIG. 1) or a K-wire (not shown). The axis of the probe 72 may be coaxial with the axis of the bore 70, and the probe 72 may be slidably received within the bore 70. In some embodiments, the probe 72 may be integrally formed as a part of the elongated rod 64.

The upper wedge 60 has an axial bore 94 for receiving the elongated rod 64. The bore 94 is dimensioned to slidably receive the elongated rod 64 such that the upper wedge 60 is slidable along and about the elongated rod 64. To that end, the upper wedge 60 is provided with a rotation member 96 to affect rotation of the upper wedge 60 in a way to facilitate neural monitoring. Generally, a user may be capable of rotating the rotation member 96 which in turn rotates the upper wedge 60. The upper wedge 60 frictionally contacts the dilator segments 16 such that rotation of the upper wedge 60 may rotate the dilator segments 16 about the elongated rod 64 (e.g., 90°).

The rotation member 96 may include an outer surface 98 and an inner surface 100. In some embodiments, the outer surface 98 may be knurled or otherwise textured to facilitate gripping of the rotation member 96. At least a portion of the inner surface 100 of the rotation member 96 may be threaded and mate with a threaded surface 104 of the upper wedge 60.

The rotation member 96 and the upper wedge 60 may form a groove 106 wherein a ring member 108 may be positioned therein. Generally, the ring member 108 remains stationary during rotation of the rotation member 96 and the upper wedge 60. For example, the ring member 108 may remain stationary when the rotation member 96, the upper wedge 60, and the dilator segments 16 rotate about the longitudinal axis of the dilator assembly 12.

As the ring member 108 may remain stationary during rotation of the rotation member 96 and the upper wedge 60, in some embodiments, the ring member 108 may further include a bearing. For example, the ring member 108 may include a bearing 110, as illustrated in FIGS. 2A and 2B. The bearing 110 may be any bearing capable of reducing friction between the ring member 108 and the upper wedge 60. For example, the bearing 110 may be a rolling element bearing, such as a ball bearing or low-frictional washers.

The actuating mechanism 14 may include an actuating handle 120. The actuating handle 120 may be detachably connected to the elongated rod 64 and the ring member 108 in suitable fashion, such as with pins 121. In some embodiments, the actuating handle 120 may be permanently attached to the elongated rod 64 and the ring member 108. Generally, the actuating handle 120 may include a first handle 122 and a second handle 124 pivotally attached to one another at a pivot point 126. Additionally, the actuating handle 120 may include a spring 128.

The handles 122 and 124 affect translation of the upper wedge 60 with respect to the lower wedge 62. In particular, the pivot point 126 provides for the second handle 124 to translate downward movement of the ring member 108. The ring member 108 in turn may displace the upper wedge 60 in a direction towards the lower wedge 62. As the distance between the upper wedge 60 and the lower wedge 62 decreases, the dilator segments 16 may be urged outwardly as the tapered surfaces 34 and 36 of the dilator segments 16 slide along the tapered surface 65 of the lower wedge 62 and the tapered surface 63 of the upper wedge 60.

Referring again to FIGS. 2A and 2B, the actuating handle 120 may include an incremental indicator 143. The incremental indicator 143 may aid in identifying expansion of the dilator assembly 12 and additionally aid in locking expansion of the dilator assembly 12 at a desired expansion. In some embodiments, the incremental indicator may be a ratchet 144 and a finger 152 capable of engaging the ratchet 144. The finger 152 may be spring-loaded and capable of incremental engagement with the ratchet 144. With the finger 152 engaged with the ratchet 144, the dilator assembly 12 is locked in a particular state (i.e., expanded state). By disengaging the finger 152 from the ratchet 144, the spring 128 may return the actuating handle 120 to a neutral position so as to return the dilator assembly 12 to the collapsed state.

In some embodiments, the ratchet 144 may include associated labels. In one example, the labels may identify the diameter of the dilator assembly 12 (e.g., 6 mm). In some embodiments, the labels may correspond to a pre-determined level of movement. For example, the labels may include a number a user will associate with a type of movement. In this example, the label "Level I" may correspond to a first expanded configuration of the dilator assembly 12, and the label "Level II" may correspond to an a second expanded configuration of the dilator assembly 12.

Figure 7:
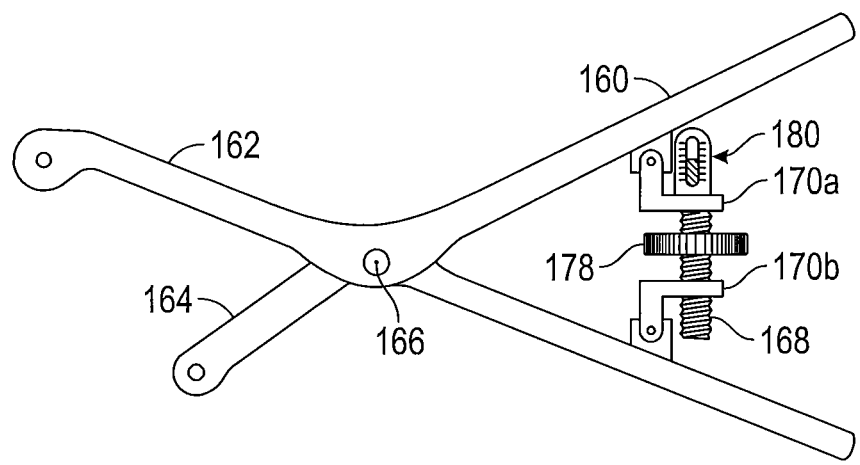
FIG. 7 a side elevational view of another embodiment of an actuating handle for use in the dilation system of FIG. 1.

FIG. 7 illustrates another exemplary actuating handle 160 for use within the dilator system 10 of FIG. 1. The actuating handle 160 may include a first handle 162 and a second handle 164 with an axis or pivot point 166. Additionally, the actuating handle 160 may include a threaded rod 168 for varying the distance between handles 162 and 164 about the pivot point 166.

The threaded rod 168 may be connected to the first handle 162 and the second handle 164 with brackets 170a and 170b, respectively. Each bracket 170a and 170b may include a hole for threading the threaded rod 168 therein. For example, a proximal end of the threaded rod 168 may be threaded through the hole of the bracket 170a, and a distal end of the threaded rod 168 may be threaded through the hole of the bracket 170b.

A knob 178 may be included on the threaded rod 168 between the brackets 170a and 170b. The knob 178 may be formed with small ridges or undulations aiding in gripping of the knob 178. Rotation of the knob 178 may increase or decrease the distance between the handles 162 and 164 about the pivot point 166.

An incremental indicator 180 may aid in identifying expansion of the dilator assembly 12 when used in the dilation system of FIG. 1. For example, two or more labels may be provided on the incremental indicator 180 to illustrate distances of expansion of the dilator assembly 12 during use as described herein.

Referring to FIGS. 2A and 2B, in use, the actuating handle 120 may be attached to the elongated rod 64 and the ring member 108, and may aid in dilating dilator segments 16 as the dilator assembly 12 is progressed up to surgical site, such as a disc annulus. The dilator segments 16 may move from the collapsed state (FIG. 2A) to the expanded state (FIG. 2B). In particular, during expansion, the actuating handle 120 may hold the elongated rod 64 substantially stationary while applying a translational force upon the ring member 108 and upper wedge 60 such that the tapered surface 34 of the inner side 32 of the dilator segments 16 slide along the tapered surface 63 of the upper wedge 60. To that end, the tapered surface 36 of the inner side 32 of the dilator segments 16 may also slide along the tapered surface 65 of the lower wedge 62 decreasing the distance between the upper wedge 60 and the lower wedge 62 and forcing the dilator segments 16 outwardly from the longitudinal axis.

In some embodiments, a K-wire (not shown) may be inserted through the bore 20 of the dilator assembly 12 to guide the dilator assembly 12 to the surgical site. In some embodiments, the K-wire may be inserted through the elongated rod 64.

Figure 8:
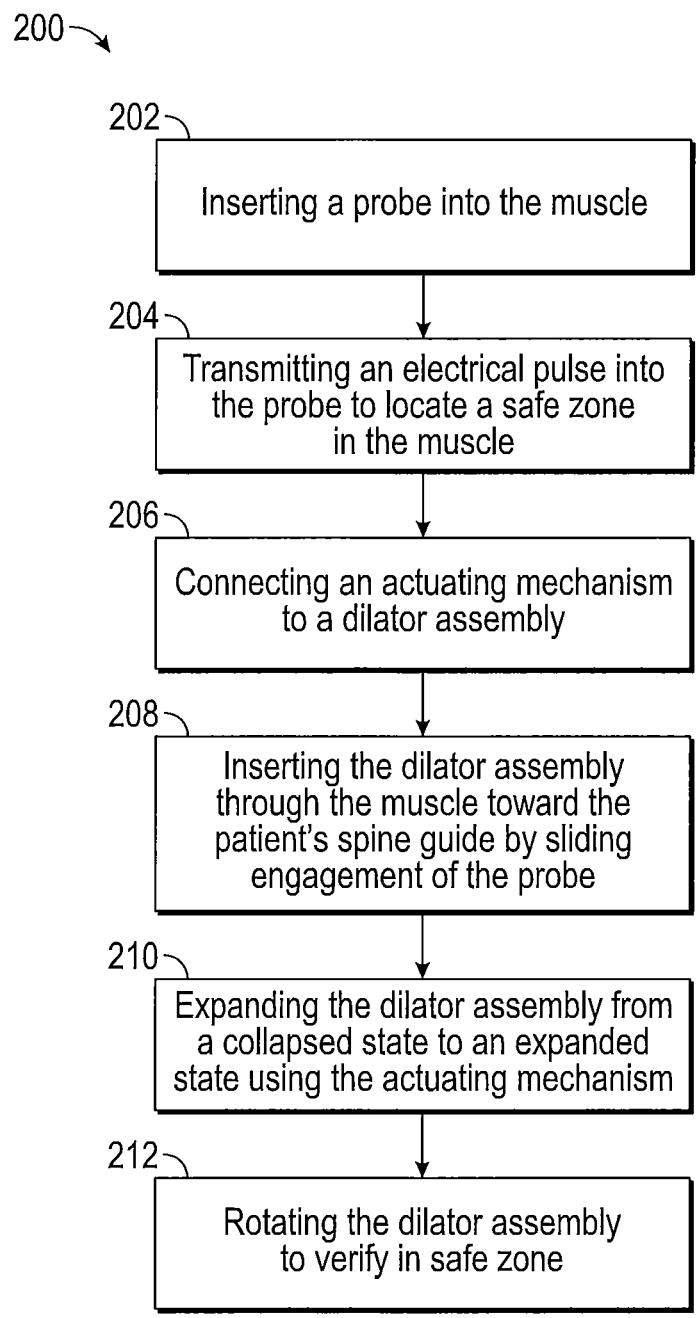
FIG. 8 is a flow chart of an exemplary method for forming an access opening through a muscle in a patient's spine.

FIG. 8 illustrates a flow chart 200 of an exemplary method for forming an access opening through a muscle in a patient's spine. In a step 202, the probe 72 or a K-wire may be inserted into the muscle. In a step 204, an electrical pulse via an electromyograph (EMG) may be transmitted into the probe 72 in order to locate a safe zone in the muscle. In a step 206, the actuating handle 120 may be connected to the dilator assembly 12 via the elongated rod 64 and the ring member 108. In a step 208, the dilator assembly 12 may be inserted through the muscle toward the patient's spine guide by the sliding engagement of the probe 72. During insertion through the muscle, the dilator assembly 12 may also use the electrode assembly 40 of the dilator assembly 12 for nerve surveillance. In some embodiments, the rotation member 96 may also provide rotation by a user such that dilator segments 16 having electrode assemblies 40 included therein may rotate about the elongated rod 64 and monitor nerves exterior to the dilator assembly 12. It should be noted that rotation of the dilator assembly 12 via the rotation member 96 is independent of the actuating handle 120.

In a step 210, the dilator assembly 12 may be incrementally expanded from the collapsed state to a desired expanded state. In particular, the distance between the upper wedge 60 and the lower wedge 62 may be decreased forcing the dilator segments 16 outwardly. In some embodiments, a user may compress the first handle 122 and the second handle 124 of the actuating handle 120. Compression of the first handle 122 and the second handle 124 may provide translational movement of the upper wedge 60 relative to the lower wedge 62 in that the proximal surface 34 of the inner side 32 of each dilator segment 16 may slidably move along the tapered surface 63 of the upper wedge 60. Additionally, the distal tapered surface 36 of the inner side 32 of each dilator segment 16 may slidably move along the tapered surface 65 of the lower wedge 62. The sliding movement of the dilator segments 16 along the tapered surfaces 65 and 63 of the lower wedge 62 and the upper wedge 60, respectively, may force the dilator segments 16 outwardly.

In a step 212, the dilator assembly 12 may be rotated via the rotation member 96 in a way to verify the dilator assembly 12 is in a safe zone. By way of example, the dilator assembly 12 may rotated through an angle of approximately 90 after each incremental increase until the dilator assembly 12 has been expanded to the desired expanded state.

To return the dilator segments 16 to a neutral position, compression of the actuating handle 120 may be reduced such that the spring 128 of the actuating handle 120 returns the upper wedge 60 to its starting position via translational movement of the ring member 108.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. A dilation system, comprising:
   a plurality of dilator segments, each dilator segment having a length, a proximal end, a distal end, an inner side, and an outer side, the dilator segments forming a tubular dilator having a longitudinal axis, at least one of the dilator segments including an electrode assembly; and
   an actuating mechanism operably associated with the dilator segments to move the dilator segments radially from a collapsed state to an expanded state,
   wherein the actuating mechanism has a rod positioned in the tubular dilator, the rod having a longitudinal bore extending therethrough, and
   wherein the dilator segments are rotatable relative to at least a portion of the actuating mechanism about the longitudinal axis.

2. The dilation system of claim 1, wherein dilator segments are rotatable relative to the rod.

3. The dilation system of claim 1, wherein the actuating mechanism includes an actuating handle, and wherein the dilator segments are rotatable relative to the actuating handle.

4. The dilation system of claim 3, wherein the actuating handle comprises:
   a first handle; and
   a second handle pivotally connected to the first handle and configured in such a way that movement of the first handle and the second handle relative to one another causes radial movement of the dilator segments.

5. The dilation system of claim 4, wherein the actuating handle includes an incremental indicator for identifying the diameter of the dilator assembly.

6. The dilation system of claim 4, wherein the actuating handle includes a ratchet having at least two teeth forming a groove, and a finger capable of being slidably received within the groove.

7. The dilation system of claim 1, wherein the dilator segments are biased in the collapsed state.

8. A dilation system, comprising:
   a plurality of dilator segments, each dilator segment having a length, a proximal end, a distal end, an inner side, and an outer side, the dilator segments forming a tubular dilator having a longitudinal axis, at least one of the dilator segments having a channel formed in the outer surface thereof and extending the length of the dilator segment for receiving a probe; and
   an actuating mechanism operably associated with the dilator segments to move the dilator segments radially from a collapsed state to an expanded state,
   wherein the actuating mechanism has a rod positioned in the tubular dilator, the rod having a longitudinal bore extending therethrough, and
   wherein the dilator segments are rotatable relative to at least a portion of the actuating mechanism about the longitudinal axis.

9. The dilation system of claim 8, wherein dilator segments are rotatable relative to the rod.

10. The dilation system of claim 8, wherein the actuating mechanism includes an actuating handle, and wherein the dilator segments are rotatable relative to the actuating handle.

11. The dilation system of claim 10, wherein the actuating handle comprises:
   a first handle; and
   a second handle pivotally connected to the first handle and configured in such a way that movement of the first handle and the second handle relative to one another causes radial movement of the dilator segments.

12. The dilation system of claim 11, wherein the actuating handle includes an incremental indicator for identifying a diameter of the dilator assembly.

13. The dilation system of claim 11, wherein the actuating handle includes a ratchet having at least two teeth forming a groove, and a finger capable of being slidably received within the groove.

14. The dilation system of claim 8, wherein the dilator segments are biased in the collapsed state.

15. A method of forming an access opening to a patient's spine, comprising the steps of:
   inserting a guide in the patient so a guide tip is proximate the patient's spine;
   inserting a dilator assembly toward the patient's spine guided by the guide, the dilator assembly comprising a plurality of dilator segments, at least one of the dilator segments having an electrode assembly;
   rotating the dilator assembly to verify a safe zone with the electrode assembly; and
   expanding the dilator segments radially from a collapsed state to an expanded state.

16. The method of claim 15, wherein the method further comprises the steps of:
   incrementally expanding the dilator assembly; and
   rotating the dilator assembly to verify the safe zone prior to each incremental expansion.

17. The method of claim 15, wherein the dilator segments form a tubular dilator having a longitudinal axis, wherein the dilator assembly has a rod positioned in the tubular dilator, the rod having a longitudinal bore extending therethrough, and wherein the method further comprises:
   rotating the dilator segments relative to the rod about the longitudinal axis.

* * * * *